United States Patent [19]

Rogers

[11] Patent Number: 5,208,145

[45] Date of Patent: May 4, 1993

[54] ASSAY FOR THE PRESENCE, IN CULTURED CELLS, OF FUNCTIONAL LIGAND-GATED CHANNELS, AND SUBSTANCES WHICH ENHANCE INTRACELLULAR LITHIUM ACCUMULATION BY CULTURED CELLS VIA SUCH CHANNELS

[75] Inventor: Scott W. Rogers, San Diego, Calif.

[73] Assignee: The Salk Institute for Biological Studies, La Jolla, Calif.

[21] Appl. No.: 695,962

[22] Filed: May 6, 1991

[51] Int. Cl.$^5$ ............... C12Q 1/68; C12Q 1/46; C12Q 1/02; G01N 33/566
[52] U.S. Cl. ............................ 435/6; 435/20; 435/29; 436/501; 436/504
[58] Field of Search .................. 435/6, 29; 436/501

[56] References Cited

PUBLICATIONS

Honchar et al., (1983) Science 220:323–325.
Aoshima (1983) J. Biochem. 94:1739–1751.
Neher et al., (1992) Scientific American Mar. 1992.

Primary Examiner—Christine M. Nucker
Assistant Examiner—David R. Preston
Attorney, Agent, or Firm—Pretty, Schroeder, Brueggemann & Clark

[57] ABSTRACT

There is provided a simple method to identify cation channels expressed in cultured cells and to screen chemical agents for their use as agonists or antagonists to such channels. In addition, the invention assay method also provides rapid means to identify cultured cell lines which express functional ion channels. The invention assay method can readily be adapted for the low cost, automated screening of potential drug materials.

20 Claims, 3 Drawing Sheets

ASSAY FOR THE PRESENCE, IN CULTURED CELLS, OF FUNCTIONAL LIGAND-GATED CHANNELS, AND SUBSTANCES WHICH ENHANCE INTRACELLULAR LITHIUM ACCUMULATION BY CULTURED CELLS VIA SUCH CHANNELS

This invention was made with Government support under Grant No. 5 RO1 NS 11549-18 awarded by the National Institute of Neurological Disorders and Stroke (NINDS). The Government has certain rights in the invention.

This invention relates to methods for screening compounds to determine if they are agonists or antagonists of cationic ligand-gated channels. This invention also relates to methods to identify cultured cell lines which express functional ion channels. In another aspect, the present invention also relates to methods to identify cation channels expressed in cultured cells.

BACKGROUND OF INVENTION

A number of pharmacologically distinct ion channels have been identified in the nervous system. For example, several distinct subunits of the neuronal receptor type have been identified. Similar observations have been made with respect to gamma-amino butyric acid (GABA), glycine, and glutamate receptor families. The pair wise expression of cloned receptor subunits in Xenopus oocytes has shown that each subtype has different pharmacological and biophysical properties. Such results suggest the degree of complexity which exists in the number of receptors that can be formed from combinations of the various receptor subunits.

One means to gain a better understanding of the pharmacology of these many ion channel subtypes is to express individual subtypes (or various combinations thereof) in cultured cells. If there were a rapid, accurate means to identify cell lines which express functional ligand-gated ion-channels, a great deal could be learned about the pharmacology of these receptor subtypes. Such a rapid, accurate assay method would also enable one to screen compounds for agonist or antagonist properties with respect to known ligand-gated, cationic channels.

SUMMARY OF THE INVENTION

In accordance with the present invention, we have developed simple assay methods which enable the rapid screening of the effect of potential agonists or antagonists on cultured cells which express ligand-gated cationic channels. The invention assay method can also be used to identify transfected cell lines which express functional ligand-gated cationic channels.

DETAILED DESCRIPTION OF THE INVENTION

Figure 1A:
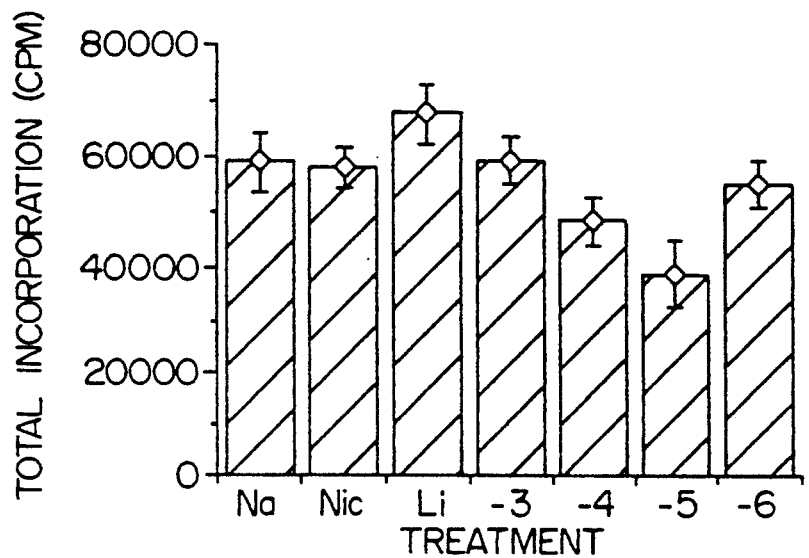
FIG. 1A contains a graphical representation of the average $^3$H-thymidine incorporation by PC12 cells when exposed to a variety of sodium- or lithium-containing buffers, in the presence or absence of nicotine.

In accordance with the present invention, there is provided a method for determining whether a compound is, directly or indirectly, an agonist or antagonist of ligand-gated channels expressed by cells. This method comprises:

measuring the incorporation of a labeled building block into said cells when said cells are contacted with an effective amount of said compound, relative to the incorporation of labeled building block into said cells when said cells are subjected to the same conditions, but in the absence of said compound;

wherein said cells have first been contacted with said compound and a lithium ion-containing flux buffer for a time sufficient to allow the intracellular accumulation of lithium, by both passive and non-passive means, but not so long as to allow the amount of passive lithium accumulation to substantially exceed the amount of non-passive lithium transport, then with an effective amount of at least one labeled cellular building block; and wherein said contacting of said cells with said labeled building block is carried out for a time sufficient to allow at least about 20% of the cell population to move from G1 phase to DNA synthesis phase, but not so long as to allow substantially all of the cell population to move from G1 phase to DNA synthesis phase.

In accordance with another embodiment of the present invention, there is provided a method for determining whether a compound is, directly or indirectly, an agonist or antagonist for ligand-gated channels expressed by cells. This method comprises:

(a) contacting said cells with an effective amount of said compound in the presence of a lithium ion-containing flux buffer for a time sufficient to allow the intracellular accumulation of lithium, by both passive and non-passive means, but not so long as to allow the amount of passive lithium accumulation to substantially exceed the amount of non-passive lithium transport, then (b) contacting said cells with an effective amount of at least one labeled cellular building block; for a time sufficient to allow at least about 20% of the cell population to move from G1 phase to DNA synthesis phase, but not so long as to allow substantially all of the cell population to move from G1 phase to DNA synthesis phase, and thereafter (c) measuring the incorporation of labeled building block into said cells, relative to the incorporation of labeled building block into said cells when subjected to at least one of the following comparative conditions:

(i) same conditions, but in the absence of said compound, or (ii) the same conditions, including the presence of said compound, but in the absence of lithium ions, or (iii) the same conditions, in the presence of said compound, and in the presence of sodium ions instead of said lithium ions.

In accordance with yet another embodiment of the present invention, there is provided a method of identifying cell(s) or cell line(s) which express functional ligand-gated channels. This method comprises:

measuring the incorporation of a labeled building block into said cell(s) or cell line(s) when said cell(s) or cell line(s) are contacted with lithium ions, relative to the incorporation of labeled building block into said cell(s) or cell line(s) when said cell(s) or cell line(s) are subjected to the same conditions, but in the absence of lithium ions;

wherein the incorporation of said labeled building block into said cell(s) or cell line(s) is determined when said cell(s) or cell line(s) are first contacted with said compound and a lithium ion-containing flux buffer for a time sufficient to allow the intracellular accumulation of lithium, by both passive and non-passive means, but not so long as to allow the amount of passive lithium accumulation to substantially exceed the amount of non-passive lithium transport, and wherein said cell(s) or cell line(s) are thereafter contacted with an effective amount of at least one labeled cellular building block; for a time sufficient to allow at least about 20% of the cell population to move from G1 phase to DNA synthesis phase, but not so long as to allow substantially all of the cell population to move from G1 phase to DNA synthesis phase.

In accordance with still another embodiment of the present invention, there is provided an alternative method of identifying cell(s) or cell line(s) which express functional ligand-gated channels. This comprises:

(a) contacting said cell(s) or cell line(s) with a lithium ion-containing flux buffer for a time sufficient to allow the intracellular accumulation of lithium, by both passive and non-passive means, but not so long as to allow the amount of passive lithium accumulation to substantially exceed the amount of non-passive lithium transport, then (b) contacting said cells with an effective amount of at least one labeled cellular building block; for a time sufficient to allow at least about 20% of the cell population to move from G1 phase to DNA synthesis phase, but not so long as to allow substantially all of the cell population to move from G1 phase to DNA synthesis phase, and thereafter (c) measuring the incorporation of labeled building block into said cell(s) or cell line(s), relative to the incorporation of labeled building block into said cell(s) or cell line(s), when said cell(s) or cell line(s) are subjected to the same conditions, but in the absence of lithium ions.

In accordance with a further embodiment of the present invention, there is provided a method to simultaneously determine if a compound is, directly or indirectly, an agonist or antagonist for ligand-gated channels contained on a cell, and if said compound has a non-specific effect on the metabolism of said cell. This method comprises:

(a) measuring the incorporation of a labeled building block into said cell(s) or cell line(s), when said cell(s) or cell line(s) have been contacted with said compound and lithium ions, relative to the incorporation of labeled building block into said cell(s) or cell line(s) when said cell(s) or cell line(s) are subjected to substantially the same conditions, but in the presence of sodium ions instead of lithium ions;

wherein the incorporation of said labeled building block into said cell(s) or cell line(s) is determined when said cell(s) or cell line(s) are first contacted with said compound and either:

a lithium ion-containing flux buffer, or a sodium ion-containing flux buffer, wherein said contacting of said cell(s) or cell line(s) with said compound and lithium or sodium ions is carried out for a time sufficient to allow the intracellular accumulation of lithium or sodium, by both passive and non-passive means, but not so long as to allow the amount of passive lithium or sodium accumulation to substantially exceed the amount of non-passive lithium or sodium transport, wherein said cell(s) or cell line(s) are thereafter contacted with an effective amount of at least one labeled cellular building block, and wherein contacting of said cell(s) or cell line(s) with said labeled cellular building block is carried out for a time sufficient to allow at least about 20% of the cell population to move from G1 phase to DNA synthesis phase, but not so long as to allow substantially all of the cell population to move from G1 phase to DNA synthesis phase; and thereafter (b) comparing the incorporation of said labeled building block into said cell(s) or cell line(s) when exposed to the presence of lithium ions, relative to the incorporation of labeled building block into said cell(s) or cell line(s) when said cell(s) or cell line(s) are exposed to sodium ions instead of lithium ions.

Compounds contemplated for testing in accordance with the present invention include any compound suspected of being an agonist or antagonist for ligand-gated ion channels, i.e., plant alkaloids, amino acids, neuro-agents, peptides, hormones, steroids, and the like. Quantities of compound employed in any of the invention assay methods can vary widely. Typically, an effective amount of test compounds will fall in the range of about 0.01 up to 1,000 $\mu$M. Exemplary test compounds include nicotine, kainic acid, and the like. When the test compound is nicotine and the ion channel being assayed is an acetylcholine receptor channel, quantities of test compound preferably fall in the range of about 1 up to 50 $\mu$M with quantities of test compound of about 10 $\mu$M being the most preferred concentration of test compound for use with such receptors. When the test compound assayed is kainic acid and the ion channel employed is a glutamate receptor channel, quantities of test compound in the range of about 100–500 $\mu$M are preferred, with quantities of about 250 $\mu$M being the presently most preferred concentration of test compound for use with such receptors.

Ligand-gated ion channels contemplated for use in the practice of the present invention are any system which will lead to enhanced intramolecular concentrations of lithium, i.e., that will depolarize under suitable conditions and allow lithium to accumulate in the cell. Examples of such ligand-gated ion channels include neuronal and muscle-type nicotinic acetylcholine receptor channels (e.g., $\alpha_2$-$\beta_2$ nAChR channels, $\alpha_3$-$\beta_2$ nAChR channels), glutamate receptor channels (e.g., GluR-K1), and the like.

Cultured cells contemplated for use in the practice of the present invention include virtually any available cell line which can be manipulated in cell culture. When $^3$H-thymidine is used as the labeled building block, any thymidine kinase positive (TK+) cell line (e.g., TK+ Rat 2 cells, PC12 cells, and the like) can be employed, with the use of dividing cells preferred. However, when labeled building blocks other than $^3$H-thymidine are employed, it is not necessary to confine the selection of host cells to thymidine kinase positive (TK+) cell lines.

Labeled building blocks contemplated for use in the practice of the present invention include labeled nucleotides and labeled amino acids. Presently preferred are radioactively labeled nucleotides or amino acids. An especially preferred labeled nucleotide is $^3$H-thymidine due to its ready availability and because this nucleotide is specific for DNA (as opposed to RNA) synthesis. Additional labeled building blocks contemplated for use in the practice of the present invention include $^{35}$S-methionine, $^3$H-leucine, and the like, including nucleotides and amino acids bearing such labels as fluorescent, chemiluminescent, or chromophoric labels.

Contacting steps contemplated by the invention assay methods comprise a lithium-flux, followed by exposure to labeled building block. To conduct the lithium-flux, culture medium is removed from the cells to be tested and gently replaced with a flux buffer, which comprises a combination of calcium chloride, glucose, HEPES (N-[2-hydroxyethyl]piperazine-N'-[2-ethanesulfonic acid]) and lithium chloride having an ionic strength compatible with continued viability of the cells being assayed.

An exemplary buffer, useful, for example, with PC12 cells, comprises:

1.8 mM calcium chloride,
25 mM glucose,
115 mM lithium chloride, and
10 mM HEPES (Ph 7.4).

As a control/comparative experiment, a flux buffer containing sodium in place of lithium is employed. An example of such a buffer comprises:

1.8 mM calcium chloride,
25 mM glucose,
115 mM sodium chloride, and
10 mM HEPES (pH 7.4).

The time-frame over which test cells are exposed to lithium-flux buffer can vary widely. Exposure time must be sufficient to allow the intracellular accumulation of lithium, by both passive and non-passive means, but not so long as to allow the amount of passive lithium accumulation to substantially exceed the amount of non-passive lithium transport. Exposure to lithium for substantially longer periods of time can result in substantial reduction in the amount of labeled building block incorporated into the cells, thereby reducing the sensitivity of the assay. Typically, contact times in the range of about 0.1-2 hours are employed, with contact times in the range of about 0.5-1 hour being presently preferred.

Cells contained in lithium-flux buffer are contacted with agonist, antagonist, or both, for an appropriate lithium-flux period at temperatures in the range of about 25°-37° C. At the conclusion of the lithium-flux period, flux buffer is removed and replaced with pre-warmed culture media containing labeled building block material. Cells are then maintained in contact with labeled building block for a time sufficient to allow at least about 20% of the cell population to move from G1 phase to the DNA synthesis phase, but not for so long a period as to allow substantially all of the cell population to move from the G1 phase to the DNA synthesis phase. If exposure time to labeled building block is too short, then the amount of labeled building block incorporated by the cell will be insufficient to provide a measurable change in incorporation, relative to cells not exposed to agonist or antagonist. Conversely, when the exposure time to labeled building block is too long, the effect of agonist or antagonist on the incorporation by the cell of labeled building block will be lessened relative to controls, presumably as a greater percentage of the cell population recovers from the transient exposure to elevated levels of lithium. Appropriate exposure time for a given cell-type can be determined by establishing the amount of time necessary for cells to move from the G1 phase to the DNA synthesis phase. It is preferred that the pulse time employed for exposure of cells to labeled building block be sufficient to allow at least about 40%, up to 60% of the cell population to move from G1 phase to the DNA synthesis phase. Typically, exposure times in the range of about 2-48 hours are suitable.

When using radiolabeled building block, labeled material with relatively low specific activity should be employed, so as to avoid levels of radioactivity that could be lethal to the cells. Typically, radiolabeled material having a specific activity in the range of about 2-5 Ci/mM be employed. Presently preferred radiolabeled material will have a specific activity of about 5 Ci/mM.

The invention will be described in greater detail by reference to the following non-limiting examples.

EXAMPLE I

Tissue Culture

PC12 cells [Greene and Tischler, Proc. Natl. Acad. Sci. USA 73: 2424-2428 (1976)] were cultured in Dulbecco's minimum essential medium (DMEM, low glucose) supplemented to 10 percent with fetal calf serum, 5 percent with heat inactivated horse serum, 5 units/ml penicillin and 5 μg/ml streptomycin. To subculture, these cells were dislodged from the culture dish by pipetting medium across the culture surface, disassociated by vigorous repeat pipetting, and then distributed to new culture dishes containing fresh media. All cells were maintained at 37° C. in a humidified atmosphere supplemented to 5 percent with $CO_2$. The PC12 cell line employed attaches to the culture dish without prior treatment of the culture surface with agents such as collagen and has been maintained in continuous culture for over one year. Northern blot analysis [Boulter et al., J. Biol. Chem. 265: 4472-4482 (1990)] of RNA obtained from this cell line indicates that the nicotinic acetylcholine receptor (nAChR) subunits expressed include alpha 3, alpha 5, beta 2 and beta 4. Alpha 2, alpha 4 and beta 3 are not detected by northern analysis. Expression of functional nicotinic AChRs was confirmed by whole cell recording as described below for transfected Rat 2 cells.

Rat 2 Cells (ATCC CRL 1764) were grown in DMEM supplemented to 5 percent with fetal bovine serum, 5 percent calf serum, and antibiotics as described above for PC12 cells. To subculture, cells were disassociated from the culture dish with trypsin/EDTA (GIBCO), resuspended in media, pelleted by centrifugation, resuspended in media, and distributed to another culture dish containing fresh media.

EXAMPLE II

Stable Transfection of Rat 2 Fibroblasts with Neuronal nAChR

The cDNA encoding the neuronal nAChR subunit alpha 2 [Wada et al., Science 24: 330–334 (1988)] was subcloned into the mammalian cell expression vector pECE [Ellis et al., Cell 45: 721–732 (1986)] which uses an SV40 early promoter and contains the SV40 polyadenylation signal. The beta 2 cDNA was subcloned into a variant of the pECE vector to which the Herpes simplex virus thymidine kinase (TK) gene [Wigler et al., Cell 14: 725–731 (1978)] was subcloned into the unique BamHI site following the poly(A) signal (pECE/TK).

Ten μg of each plasmid DNA was mixed and introduced into cultured Rat 2 cells by the calcium phosphate precipitation method [Wigler et al., supra]. Plasmid DNA was left on cells for 14 hours, the cells were rinsed with PBS, the culture medium replaced, and culture continued for 48 hours. At this time, culture medium was supplemented to 16 μM thymidine, 100 μM hypoxanthine, and 400 nM aminopterin (HAT medium). After two weeks, clonal TK cell colonies were individually removed by trypsinization and expanded. Clonal cell lines were maintained in HAT medium and were screened for the expression of functional nAChRs by the lithium-flux method and by immunoprecipitation as described below. As a control, one Rat 2 cell line was chosen that had been stably transfected with only the beta 2-pECE/TK plasmid and could grow in HAT medium.

EXAMPLE III

Lithium-flux and Cell Harvestino

PC12 cells were distributed to 96 well Costar culture dishes ($10^4$ cells/well) and the cells were allowed to recover for 24 to 36 hours prior to use. Cells were never allowed to reach confluency. To conduct a lithium-flux experiment, the culture medium was removed and gently replaced with flux-buffer composed of 1.8 mM $CaCl_2$, 25 mM glucose, 10 mM HEPES (pH 7.4), and 115 mM in either sodium chloride or lithium chloride. Each buffer was filter sterilized and supplemented with agonist, antagonist, or both, as described for the experiment being conducted. Cells were returned to 37° C. for a 30 minute flux period whereupon the flux buffer was removed and replaced with pre-warmed culture media containing enough $^3$H-thymidine to make a final concentration of 0.5 μCi per well. For PC12 cells, culture was then continued as usual for 6 hours before quantitating $^3$H-thymidine incorporation. Transfected cells were subjected to a pulse period of 16 hours before harvest. In all experiments, each treatment was done simultaneously in six wells of one column of the culture dish. The outer rows and columns were filled with culture medium but were not used for cell culture.

To determine the incorporation of $^3$H-thymidine into fluxed cells, dishes were frozen at −70°, thawed, and the DNA from each well was collected on glass filters using a Cambridge PhD cell harvester. Although PC12 cells dislodged easily following thawing, transfected cells often required an additional treatment with 0.5 N sodium hydroxide before harvesting. Glass filters were dried, resuspended in Ecolume (ICN) scintillation cocktail, and counted in an LKB Wallace 2010 scintillation counter at 34 percent efficiency. Results were calculated by averaging the total counts from six wells and then comparing these to the experimental controls (sodium flux-buffer with and without agonist (and/or antagonist) and lithium flux-buffer without agonist (and/or antagonist). To compare results between experiments, the total counts in each control sample was normalized to 100 and the remaining values adjusted accordingly. In one experiment flame emission atomic absorption spectroscopy was used to confirm that lithium ions were fluxed into cells.

Figure 1B:
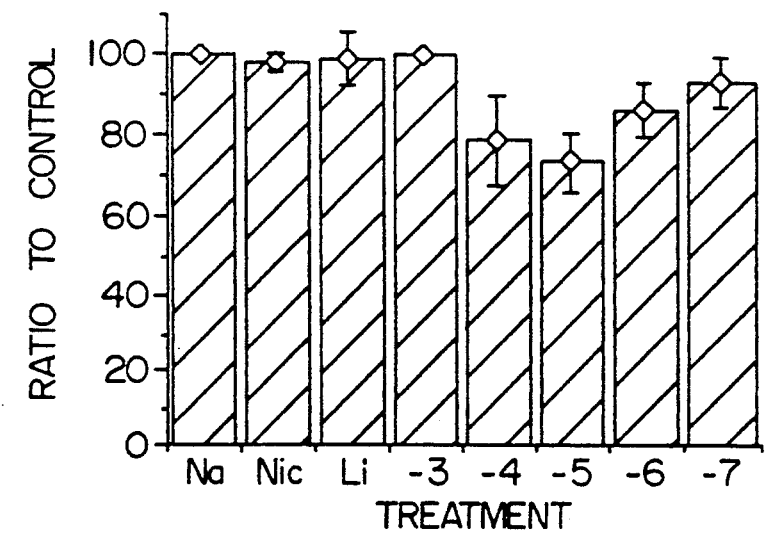
FIG. 1B contains a graphical representation of the average $^3$H-thymidine incorporation by PC12 cells when exposed to a variety of medium- or lithium-containing buffers, in the presence or absence of nicotine, where the total count in each sample is normalized to the control valve of 100.

The average $^3$H-thymidine incorporation (and the ratio of incorporation relative to control) from six wells is shown in FIG. 1 for each of several treatments. "Na" refers to a test run with sodium formulated buffer plus 10 μM nicotine: "Nic" refers to a test run with lithium formulated buffers and 10 μm nicotine; "Li" refers to a test run with lithium formulated buffer; "−3 to −7" refer to test runs employing lithium formulated buffer containing 1 mM, 100 μM, 10 μM, 1 μM, and 0.1 μM nicotine, respectively. Standard error of the mean is indicated by the vertical bars.

This experiment demonstrates that the optimal nicotine concentration for activating nicotine acetylcholine receptors, as traditionally determined by electrophysiology [see, for example, Luetje and Patrick, J. Neurosci. 11: 837–845 (1991)], can also be determined by use of the invention lithium flux assay. In addition, this experiment demonstrates that the presence of nicotine does not alter the cell cycle time of PC12 cells.

Figure 2:
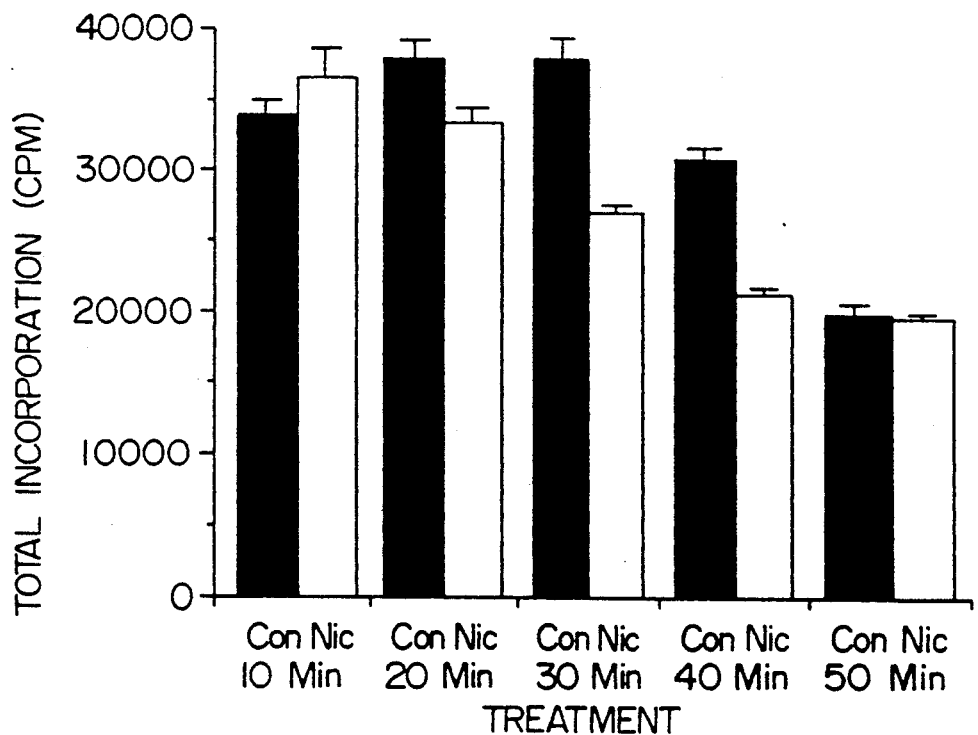
FIG. 2 graphically illustrates the effect of the duration of the lithium flux step on the incorporation of labeled building block by PC12 cells.

The optimal lithium flux period can readily be determined, as illustrated in FIG. 2 for PC12 cells. Cells were prepared as described above and treated with either lithium formulated buffer (Con) or lithium formulated buffer and 10 μM nicotine (Nic) for 10, 20, 30, 40, or 50 minutes. $^3$H-thymidine containing DMEM was added for 6 hours and the DNA harvested as described above. Results are reported as the total $^3$H-thymidine incorporated.

This experiment demonstrates that there is an optimal time for which cells will preferably reside in the lithium-containing buffer in order to ensure that the effect of lithium incorporation on the cells will be observed. If the residence time in the lithium-containing buffer is too short, then, during agonist stimulation, an insufficient amount of lithium will be fluxed through the channel to exceed the threshold where incorporation of metabolic label is measurably affected. Conversely, if the residence time in the lithium-containing buffer is too long, then the lithium threshold for inhibiting metabolic processes will be exceeded independently of the presence of a ligand-gated ion channel. The results of this experiment indicate that the preferred lithium exposure time for PC12 cells is about 10 minutes, which is ample time for the handling required to carry out the invention procedure.

Figure 3:
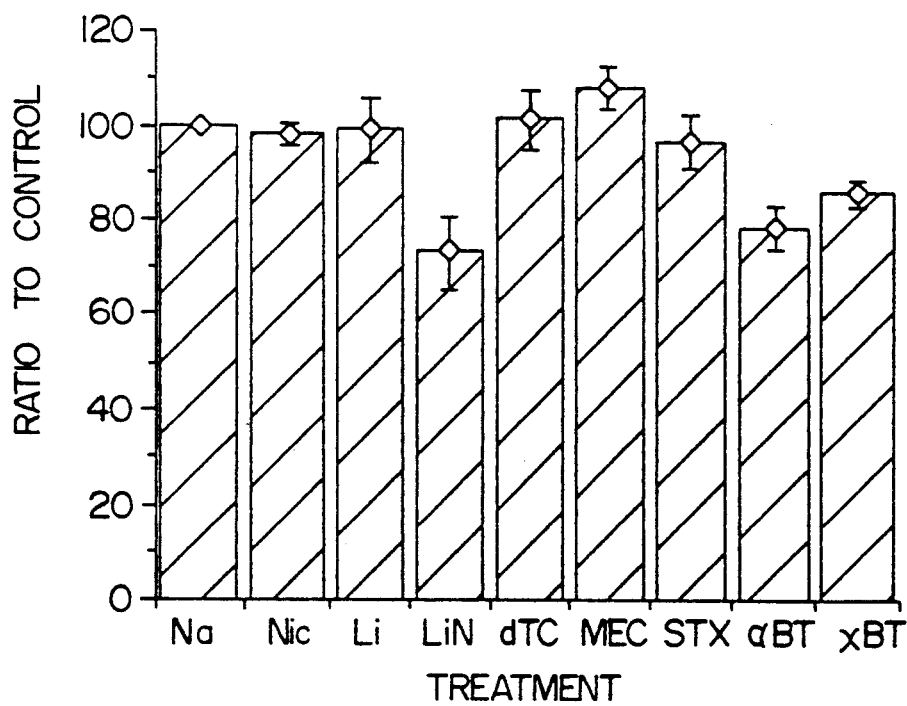
FIG. 3 illustrates the effect of potential neuronal acetylcholine receptor (nAChR) antagonists on PC12 cells.

FIG. 3 illustrates the effect of potential nAChR antagonists on PC12 cells. "Na" refers to a test run with sodium-formulated buffer; "Nic" refers to a test run with sodium formulated buffer plus 10 μM nicotine; "Li" refers to a test run with lithium formulated buffer; "LiN" refers to a test run with lithium formulated buffer containing 10 μM nicotine; "dTC" refers to a test run with lithium formulated buffer containing 10 μM and 10 mM d-tubocurarine; "MEC" refers to a test run with lithium formulated buffer containing 10 μM nicotine and 10 μM mecamylamine; "STX" refers to a test run with lithium formulated buffer containing 10 μM nicotine and 5 nM neosurogatoxin; "αBT" refers to a test run with lithium formulated buffer containing 10 μM nicotine and 100 nM alpha bungarotoxin; and "kBT" refers to a test run with lithium formulated buffer containing 10 μM nicotine and 100 nM kappa-bungarotoxin. The data are normalized to the control value (Na) of 100.

This experiment demonstrates that the correct pharmacology for the nicotinic acetylcholine receptor, as determined by electrophysiology [see, for example, Leutje et al., J. Neurochem. 55: 632–640 (1990)], can also be readily determined employing the invention lithium-flux assay method.

Figure 4:
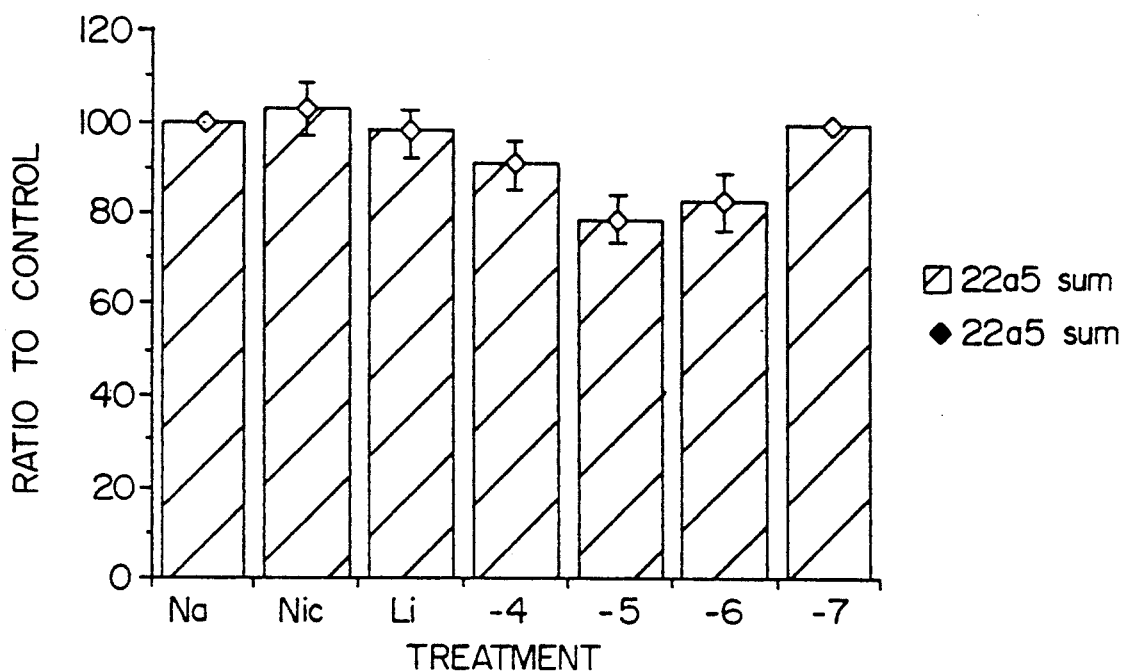
FIG. 4 contains a graphical representation of the average $^3$H-thymidine incorporation by transfected Rat 2 cells when exposed to a variety of sodium- or lithium-containing buffers in the presence or absence of nicotine.

FIG. 4 presents the results of lithium flux of a Rat 2 cell line stably transfected with cDNAs encoding the neuronal nicotinic acetylcholine receptor subunits alpha 2 and beta 2, respectively. RAT 2 cells (TK⁻ phenotype) were cotransfected with cDNAs encoding the Herpes simplex thymidine kinase gene, and the neuronal nAChR subunits alpha 2 and beta 2 as described above. For one of these cell lines, 22A5, the sum of 9 different experiments is shown where the total counts were normalized to the control (Na) value of 100. "Na" refers to a test run with sodium formulated buffer; "Nic" refers to a test run with sodium formulated buffer plus 10 μM nicotine; "Li" refers to a test run with lithium formulated buffer; "−4 to −7" refer to test runs employing lithium formulated buffer containing 100 μM, 10 μM, 1 μM, and 0.1 μM nicotine, respectively.

This experiment demonstrates that the optimal nicotine concentration for activating nicotine acetylcholine receptors, as determined by electrophysiology [see, for example, Leutje and Patrick, supra], can readily be obtained by the invention lithium flux method with Rat 2 fibroblasts (which have been transfected with subunits to express functional nicotinic acetylcholine receptors of desired subunit composition).

Figure 5:
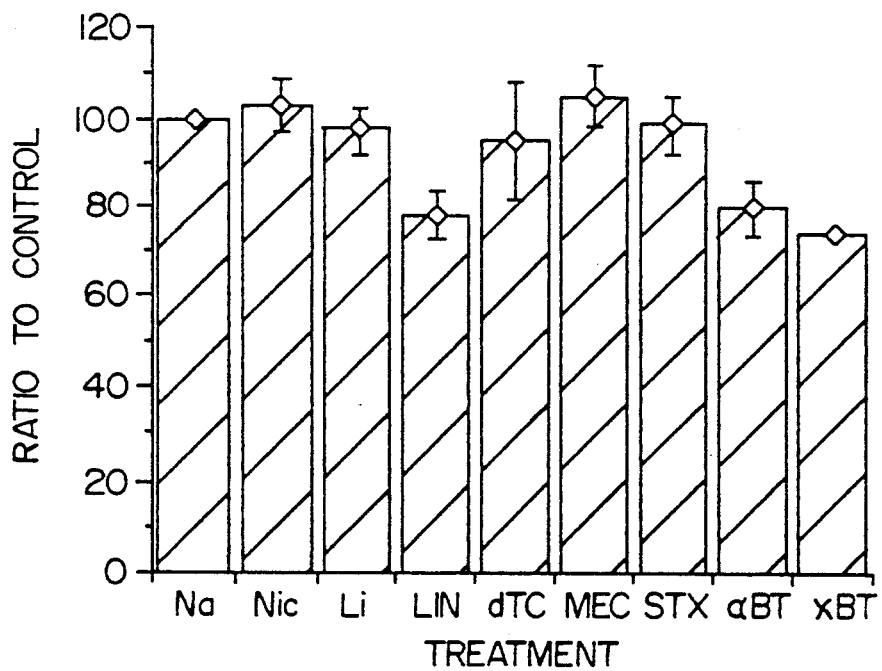
FIG. 5 illustrates the effect of potential neuronal acetylcholine receptor (nAChR) antagonists on transfected Rat 2 cells.

FIG. 5 presents the effect of potential nAChR antagonists on the transfected Rat 2 cell line, 22A5. "Na" refers to a test run with sodium-formulated buffer; "Nic" refers to a test run with sodium formulated buffer plus 10 μM nicotine; "Li" refers to a test run with lithium formulated buffer; "LiN" refers to a test run with lithium formulated buffer containing 10 μM nicotine; "dTC" refers to a test run with lithium formulated buffer containing 10 μM nicotine and 10 mM d-tubocurarine; "MEC" refers to a test run with lithium formulated buffer containing 10 μM nicotine and 10 μM mecamylamine; "STX" refers to a test run with lithium formulated buffer containing 10 μM nicotine and 5 nM neosurogatoxin; "αBT" refers to a test run with lithium formulated buffer containing 10 μM nicotine and 100 nM alpha-bungarotoxin; and "kBT" refers to a test run with lithium formulated buffer containing 10 μM nicotine and 100 nM kappa-bungarotoxin. The data are normalized to the control value (Na) of 100.

EXAMPLE IV

Electrophysiology

Transfected cells were cultured in 35 mm tissue culture dishes as described above. To enhance expression of nAChR subunits [see Leutje et al., supra], 10 mM sodium butyrate [Claudio et al., Science 238: 1688–1694 (1987)] was added to the culture medium 48 hours prior to recording. At this time cells which had become rounded with a 'spider-like' morphology were tested for their response to acetylcholine. Recordings were obtained on cells at room temperature using the whole cell patch-clamp configuration and a Daga 8900 patch-clamp amplifier (0.1 G-ohm probe). Pipettes were made from borosilicate glass (Dagen Corp., LE-16) and coated within 100 μm of the tip with Sylgard. The initial resistance of fire-polished pipettes ranged from 4 to 8 megaOhms. The patch pipette contained 133 mM KCl, 1 mM CaCl$_2$, and 10 mM HEPES (pH 7.3). Control bath solution and bath solution containing agonist were delivered to the cell with a modified version of the U-tube fast perfusion device [Magazanik and Vyskocil, Eur. J. Physiol. 391: 85–100 (1981)]. Solutions passed by gravity flow through PE10 tubing into and out of the pipette. Flow was regulated by an electronic switch allowing the stream of solution to be directed at the cell with a latency of approximately 100 msec. Current responses were digitized (modified Sony model 701-ES PCN) and recorded onto video tape for later analysis.

EXAMPLE V

Immunoprecipitation

The presence of neuronal nAChR subunit protein in transfected Rat 2 cells was confirmed by immunoprecipitation with subunit specific antibodies to the alpha 2 and beta 2 subunits. The trpE bacterial over-expression system [Dieckmann and Tzagoloff, J. Biol. Chem. 260: 1513–1520 (1985)] was used to express portions of the putative cytoplasmic domains of alpha 2 (residues 71–511) and beta 2 (residues 394–503). See Wada et al., supra and Deneris et al., J. Biol. Chem. 264: 6268–6272 (1989), from which the preceding residue numbers were obtained. These fusion proteins were partially purified by high salt precipitation [Dieckmann and Tzagoloff, supra] and fractionated using sodium dodecylsulfate-polyacrylamide gel electrophoresis (SDS-PAGE). The fusion protein was visualized by soaking the gel in 0.25 M KCl for 30 minutes at 4° C. and these regions of the gel were removed, macerated, emulsified in Freund's complete adjuvant and injected subcutaneously into New Zealand white rabbits. Four weeks later rabbits were boosted with antigen prepared as above but emulsified in incomplete Freund's adjuvant. Two weeks later serum was collected subsequent to ear bleeding and the antiserum was tested for immunoreactivity to over-produced protein by Western blot analyses [Kyse-Andersen, J. Biochem. Biophys. Methods 10: 203–204 (1984)].

For immunoprecipitations, cultured cells were grown in HAT medium supplemented to 10 mM with sodium butyrate, which increases transcription from the SV40 promoter [see Claudio et al., supra] for 24 hours. This medium was removed and HAT medium lacking methionine and supplemented to 3 percent dialyzed fetal bovine serum (GIBCO), 10 mM sodium butyrate and 100 uCi/ml $^{35}$S-translabel (ICN) was then added and culture continued for 16 to 18 hours. This medium was removed, the cells were washed in PBS and then scraped with a rubber policeman from the culture dish in solubilization buffer (50 mM Tris, pH 8.5, 1 mM EDTA, 1 mM ESTA, 5 mM iodoacetimide, 5 mM benzamidine, 1 mM phenylmethylsulfonyl fluoride (PMSF) and 2% Triton X-100). Cell extracts were cleared by centrifugation in an Eppendorf centrifuge, pre-immune serum (1:300) was added to the supernatants and they were rocked overnight at 4° C. Ten μL of Pansorbin (Calbiochem) was then added to the rocking tube for 1 hour at room temperature before clearing by centrifugation. Immune serum was added to these supernatants, and rocking was continued for 5 hours at room temperature before adding Pansorbin as above. This pellet was then washed with 50 mM Tris, pH 7.5, the pellet was dissolved by boiling in SDS-PAGE sample buffer [Laemmli, Nature 227: 680–685 (1979)], and the proteins fractionated by SDS-PAGE. Gels were then stained, destained, dried, and exposed to X-OMAT AR X-Ray film (Kodak) for various times at −70° C.

While the invention has been described in detail with reference to certain preferred embodiments thereof, it will be understood that modifications and variations are within the spirit and scope of that which is described and claimed.

That which is claimed is:

1. A method for determining whether a compound is, directly or indirectly, an agonist or antagonist of ligand-gated channels expressed by cells, said method comprising:
   measuring the incorporation of a labeled building block into said cells when said cells are contacted with an effective amount of said compound, relative to the incorporation of labeled building block into said cells when said cells are subjected to the same conditions, but in the absence of said compound;
   wherein said cells have first been contacted with said compound and a lithium ion-containing flux buffer for a time sufficient to allow the intracellular accumulation of lithium, by both passive and non-passive means, but not so long as to allow the amount of passive lithium accumulation to substantially exceed the amount of non-passive lithium transport, then with an effective amount of at least one labeled cellular building block; and
   wherein said contacting of said cells with said labeled building block is carried out for a time sufficient to allow at least about 20% of the cell population to move from G1 phase to DNA synthesis phase, but not so long as to allow substantially all of the cell population to move from G1 phase to DNA synthesis phase.

2. A method according to claim 1 wherein said effective amount of said compound falls in the range of about 0.01 up to 1,000 μM.

3. A method according to claim 2 wherein said compound is nicotine and said channel is an acetylcholine receptor channel.

4. A method according to claim 3 wherein said effective amount of said compound falls in the range of about 1 up to 50 μM.

5. A method according to claim 2 wherein said compound is kainic acid and said channel is a glutamate receptor channel.

6. A method according to claim 5 wherein said effective amount of said compound falls in the range of about 100 up to 500 μM.

7. A method according to claim 1 wherein said lithium ion-containing flux buffer comprises a combination of calcium chloride, glucose, HEPES and lithium chloride having an ionic strength compatible with continued viability of the cells being assayed.

8. A method according to claim 7 wherein said flux buffer comprises:
   1.8 mM calcium chloride,
   25 mM glucose,
   115 mM lithium chloride, and
   10 mM HEPES (pH 7.4).

9. A method according to claim 7 wherein the time sufficient to allow the intracellular accumulation of lithium, by both passive and non-passive means, falls in the range of about 0.1 up to 2 hours.

10. A method according to claim 1 wherein said labeled building block is a radioactively labeled nucleotide or a radioactively labeled amino acid.

11. A method according to claim 10 wherein the pulse time for said labeled building block is sufficient to allow at least about 40%, up to about 60%, of the cell population to move from G1 phase to DNA synthesis phase.

12. A method according to claim 10 wherein the pulse time for said labelled building block falls in the range of about 2 up to 48 hours.

13. A method according to claim 11 wherein said labeled building block is a radioactively labeled nucleotide, and wherein said radioactively labeled nucleotide is present in an amount sufficient to allow quantities, adequate for measurement of said labeled nucleotide, to be incorporated into said cell, during said flux period.

14. A method according to claim 13 wherein said radioactively labeled nucleotide is present in an amount in the range of about 1 up to 50 μCi/ml of analysis solution.

15. A method according to claim 10 wherein said measuring of the incorporation of a labeled building block into said cells is carried out by determining the number of counts per unit time emitted by the sample.

16. A method for determining whether a compound is, directly or indirectly, an agonist or antagonist for ligand-gated channels expressed by cells, said method comprising:
   (a) contacting said cells with an effective amount of said compound in the presence of a lithium ion-containing flux buffer for a time sufficient to allow the intracellular accumulation of lithium, by both passive and non-passive means, but not so long as to allow the amount of passive lithium accumulation to substantially exceed the amount of non-passive lithium transport, then
   (b) contacting said cells with an effective amount of at least one labeled cellular building block; for a time sufficient to allow at least about 20% of the cell population to move from G1 phase to DNA synthesis phase, but not so long as to allow substantially all of the cell population to move from G1 phase to DNA synthesis phase, and thereafter
   (c) measuring the incorporation of labeled building block into said cells, relative to the incorporation of labeled building block into said cells when subjected to at least one of the following comparative conditions:
      (i) the same conditions, but in the absence of said compound, or
      (ii) the same conditions, including the presence of said compound, but in the absence of lithium ions, or
      (iii) the same conditions, in the presence of said compound, and in the presence of sodium ions instead of said lithium ions.

17. A method of identifying cell(s) or cell line(s) which express functional ligand-gated channels, said method comprising:
   measuring the incorporation of a labeled building block into said cell(s) or cell line(s) when said cell(s) or cell line(s) are contacted with lithium ions, relative to the incorporation of labeled building block into said cell(s) or cell line(s) when said cell(s) or cell line(s) are subjected to the same conditions, but in the absence of lithium ions;

wherein the incorporation of said labeled building block into said cell(s) or cell line(s) is determined when said cell(s) or cell line(s) are first contacted with said compound and a lithium ion-containing flux buffer for a time sufficient to allow the intracellular accumulation of lithium, by both passive and non-passive means, but not so long as to allow the amount of passive lithium accumulation to substantially exceed the amount of non-passive lithium transport, and wherein said cell(s) or cell line(s) are thereafter contacted with an effective amount of at least one labeled cellular building block; for a time sufficient to allow at least about 20% of the cell population to move from G1 phase to DNA synthesis phase, but not so long as to allow substantially all of the cell population to move from G1 phase to DNA synthesis phase.

18. A method of identifying cell(s) or cell line(s) which express functional ligand-gated channels, said method comprising:

(a) contacting said cell(s) or cell line(s) with a lithium ion-containing flux buffer for a time sufficient to allow the intracellular accumulation of lithium, by both passive and non-passive means, but not so long as to allow the amount of passive lithium accumulation to substantially exceed the amount of non-passive lithium transport, then (b) contacting said cells with an effective amount of at least one labeled cellular building block; for a time sufficient to allow at least about 20% of the cell population to move from G1 phase to DNA synthesis phase, but not so long as to allow substantially all of the cell population to move from G1 phase to DNA synthesis phase, and thereafter (c) measuring the incorporation of labeled building block into said cell(s) or cell line(s), relative to the incorporation of labeled building block into said cell(s) or cell line(s), when said cell(s) or cell line(s) are subjected to the same conditions, but in the absence of lithium ions.

19. A method to simultaneously determine if a compound is, directly or indirectly, an agonist or antagonist for ligand-gated channels contained on a cell, and if said compound has a non-specific effect on the metabolism of said cell, said method comprising:

(a) measuring the incorporation of a labeled building block into said cell(s) or cell line(s), when said cell(s) or cell line(s) have been contacted with said compound and lithium ions, relative to the incorporation of labeled building block into said cell(s) or cell line(s) when said cell(s) or cell line(s) are subjected to substantially the same conditions, but in the presence of sodium ions instead of lithium ions;

wherein the incorporation of said labeled building block into said cell(s) or cell line(s) is determined when said cell(s) or cell line(s) are first contacted with said compound and either:

a lithium ion-containing flux buffer, or
a sodium ion-containing flux buffer, wherein said contacting of said cell(s) or cell line(s) with said compound and lithium or sodium ions is carried out for a time sufficient to allow the intracellular accumulation of lithium or sodium, by both passive and non-passive means, but not so long as to allow the amount of passive lithium or sodium accumulation to substantially exceed the amount of non-passive lithium or sodium transport, wherein said cell(s) or cell line(s) are thereafter contacted with an effective amount of at least one labeled cellular building block, and wherein contacting of said cell(s) or cell line(s) with said labeled cellular building block is carried out for a time sufficient to allow at least about 20% of the cell population to move from G1 phase to DNA synthesis phase, but not so long as to allow substantially all of the cell population to move from G1 phase to DNA synthesis phase; and thereafter (b) comparing the incorporation of said labeled building block into said cell(s) or cell line(s) when exposed to the presence of lithium ions, relative to the incorporation of labeled building block into said cell(s) or cell line(s) when said cell(s) or cell line(s) are exposed to sodium ions instead of lithium ions.

20. A method according to claim 19 wherein said lithium ion-containing flux buffer comprises a combination of calcium chloride, glucose, HEPES and lithium chloride having an ionic strength compatible with continued viability of the cells being assayed, and wherein said sodium ion-containing flux buffer comprises a combination of calcium chloride, glucose, HEPES and sodium chloride having an ionic strength compatible with continued viability of the cells being assayed.

* * * * *